United States Patent
Koenig et al.

(10) Patent No.: US 8,811,662 B2
(45) Date of Patent: Aug. 19, 2014

(54) METHOD AND APPARATUS FOR CALIBRATING AND RE-ALIGNING AN ULTRASOUND IMAGE PLANE TO A NAVIGATION TRACKER

(75) Inventors: Matthew W. Koenig, Dacono, CO (US); Danail G. Danailov, Westminster, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 227 days.

(21) Appl. No.: 13/097,264

(22) Filed: Apr. 29, 2011

(65) Prior Publication Data

US 2012/0275645 A1    Nov. 1, 2012

(51) Int. Cl.
*G06K 9/00*    (2006.01)

(52) U.S. Cl.
USPC ............................. 382/103; 382/128; 382/151

(58) Field of Classification Search
USPC .......................................... 382/103, 128, 151
See application file for complete search history.

(56) References Cited

U.S. PATENT DOCUMENTS

| | | |
|---|---|---|
| 5,040,225 A | 8/1991 | Gouge |
| 5,592,939 A | 1/1997 | Martinelli |
| 5,983,126 A | 11/1999 | Wittkampf |
| 6,138,495 A | 10/2000 | Paltieli et al. |
| 6,379,302 B1 | 4/2002 | Kessman et al. |
| 6,474,341 B1 | 11/2002 | Hunter et al. |
| 6,747,539 B1 | 6/2004 | Martinelli |
| 6,775,404 B1 | 8/2004 | Pagoulatos et al. |
| 6,940,941 B2 | 9/2005 | Gregerson et al. |
| 7,001,045 B2 | 2/2006 | Gregerson et al. |
| 7,085,400 B1 | 8/2006 | Holsing et al. |
| 7,106,825 B2 | 9/2006 | Gregerson et al. |
| 7,108,421 B2 | 9/2006 | Gregerson et al. |
| 7,188,998 B2 | 3/2007 | Gregerson et al. |
| 7,751,865 B2 | 7/2010 | Jascob et al. |
| 7,797,032 B2 | 9/2010 | Martinelli et al. |
| 7,831,082 B2 | 11/2010 | Holsing et al. |
| 2004/0097805 A1* | 5/2004 | Verard et al. .................. 600/428 |
| 2004/0116803 A1 | 6/2004 | Jascob et al. |
| 2004/0199072 A1 | 10/2004 | Sprouse et al. |
| 2006/0034513 A1* | 2/2006 | Cai et al. ........................ 382/173 |
| 2006/0036170 A1* | 2/2006 | Lachaine et al. .............. 600/437 |
| 2007/0167787 A1 | 7/2007 | Glossop et al. |

(Continued)

FOREIGN PATENT DOCUMENTS

| | | |
|---|---|---|
| DE | 20204003757 | 5/2004 |
| EP | 1779786 A1 | 5/2007 |
| WO | WO-2012149357 A1 | 11/2012 |
| WO | WO-2012149370 A1 | 11/2012 |

OTHER PUBLICATIONS

"AxiEM Electromagetic Navigation," tri-fold brochure, Medtronic Navigation (2005) 2 pages.

(Continued)

*Primary Examiner* — Matthew Bella
*Assistant Examiner* — Weiwen Yang
(74) *Attorney, Agent, or Firm* — Harness, Dickey

(57) ABSTRACT

The present disclosure relates to acquiring image data of a subject with an imaging system that has been calibrated. The imaging system can include an ultrasound imaging system that collects one or more images based on a plane of image acquisition. The plane of image acquisition can be calibrated to a tracking device associated with the ultrasound transducer.

14 Claims, 10 Drawing Sheets

(56) References Cited

U.S. PATENT DOCUMENTS

| | | |
|---|---|---|
| 2008/0119712 A1* | 5/2008 | Lloyd .......................... 600/407 |
| 2010/0228117 A1 | 9/2010 | Hartmann |
| 2011/0052008 A1 | 3/2011 | Holsing et al. |
| 2012/0275645 A1 | 11/2012 | Koenig et al. |
| 2012/0277585 A1 | 11/2012 | Koenig et al. |

OTHER PUBLICATIONS

"Mayfield® Skull Clamps and Headrest Systems," Mayfield® Surgical Devices Product Index, pp. 1-6, December, 2004 Integra LifeSciences Corporation.

"StealthStation_S7_System® Information Center in the OR," (2009) Medtronic, Inc.

"StealthStation® TRIA™ plus Treatment Guidance System," brochure, Medtronic Surgical Navigation Technologies (2004) 2 pages.

"TREON, StealthStation," brochure, Medtronic Surgical Navigation Technologies (2001) 8 pages.

International Search Report and Written Opinion mailed Jul. 11, 2012 for PCT/US2012/035503 claiming benefit of U.S. Appl. No. 13/097,253, filed Apr. 29, 2011.

International Search Report and Written Opinion mailed Jul. 6, 2012 for PCT/US2012/035522 claiming benefit of U.S. Appl. No. 13/097,264, filed Apr. 29, 2011.

Mercier, L, et al., "A review of calibration techniques for freehand 3-D ultrasound systems", Ultrasound in Medicine and Biology, New York, NY, US, vol. 31, No. 2, Feb. 1, 2005, pp. 143-165.

International Preliminary Report on Patentability and Written Opinion mailed Nov. 7, 2013 for PCT/US2012/035503 claiming benefit of U.S. Appl. No. 13/097,253, filed Apr. 29, 2011.

International Preliminary Report on Patentability and Written Opinion mailed Nov. 7, 2013 for PCT/US2012/035522 claiming benefit of U.S. Appl. No. 13/097,264, filed Apr. 29, 2011.

* cited by examiner

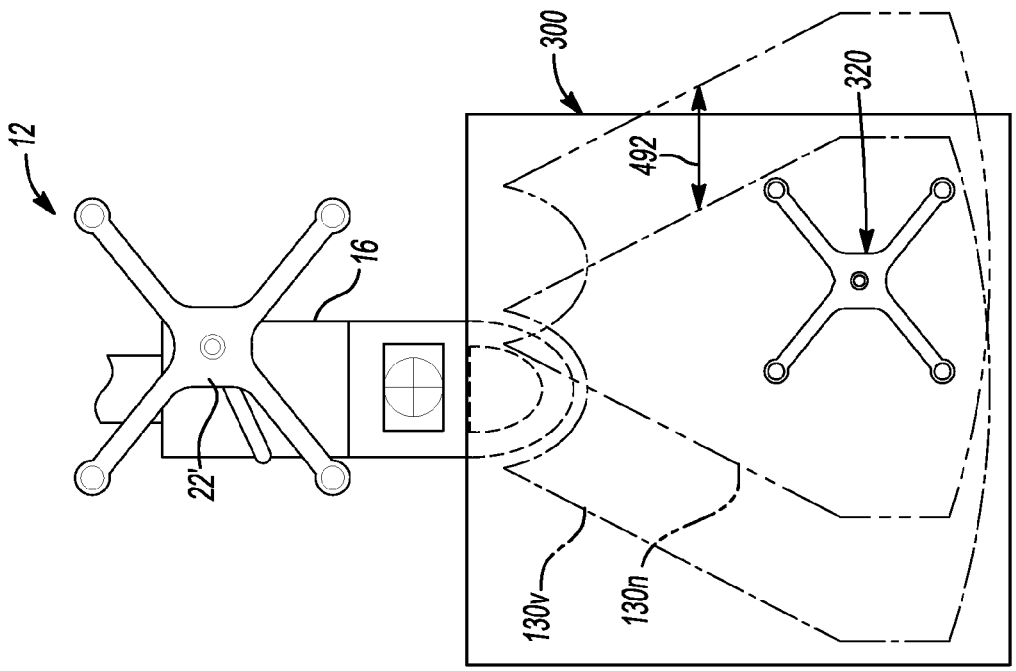
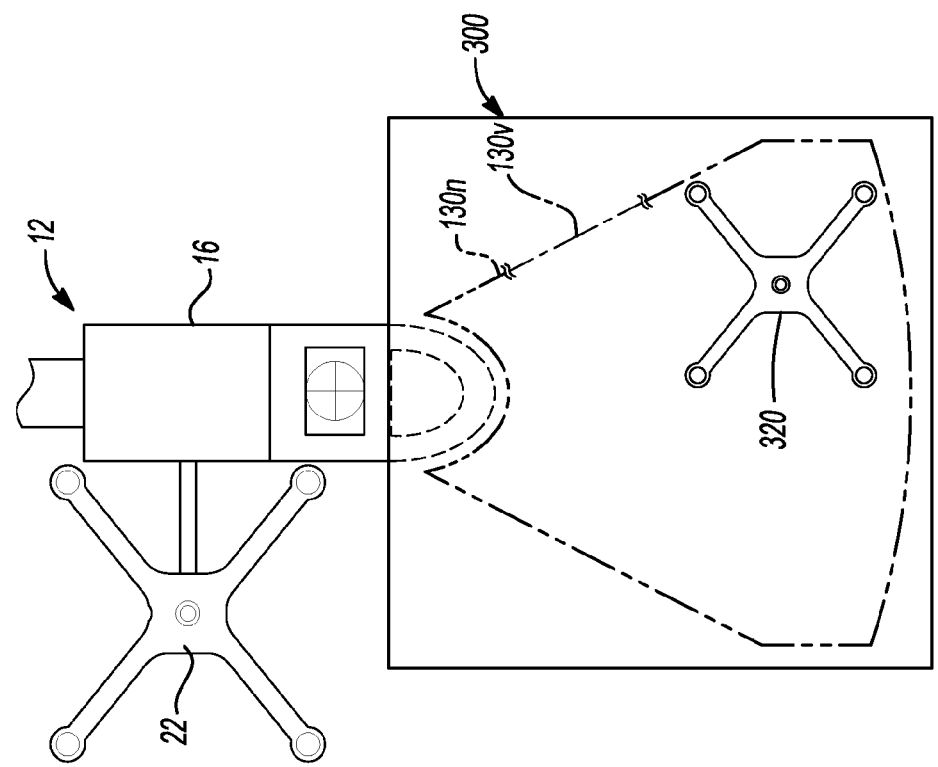

METHOD AND APPARATUS FOR CALIBRATING AND RE-ALIGNING AN ULTRASOUND IMAGE PLANE TO A NAVIGATION TRACKER

CROSS-REFERENCE TO RELATED APPLICATIONS

This application also includes subject matter related to U.S. patent application Ser. No. 13/097,253, filed concurrently with this application. The disclosure of the above application is incorporated herein by reference.

FIELD

The present disclosure relates to acquisition of image data of a subject, and particularly to acquisition and display of image data collected from a calibrated and tracked imaging system.

BACKGROUND

This section provides background information related to the present disclosure which is not necessarily prior art.

An imaging system can be used to image various portions of a subject. The subject can include a patient, such as a human patient. The portions selected to be imaged can be internal portions that are covered by skin or other tissue. However, a location of portions of the subject that are imaged may be selected to be known. The locations can be locations relative to instruments placed in the subject (e.g. a location of a catheter relative to a heart wall) or a location of the imaged portion relative the instrument acquiring the image data.

SUMMARY

This section provides a general summary of the disclosure, and is not a comprehensive disclosure of its full scope or all of its features.

A calibration device or jig can be used to determine the locations with an image, such as within an image plane of an ultrasound (US) imaging device, by imaging portions of the calibration jig that are at known locations. The calibration jig can be tracked with a tracking system as can the US transducer or a housing containing the US transducer. The US transducer generates US waves that are used to generate or produce an image plane. If portions of the calibration jig are at known locations relative to the tracked calibration jig, then identifying the locations of the imaged portions within the image plane can be used to calibrate locations within the image plane to the US transducer. This allows for portions imaged with the US transducer after calibration to be located with a tracking system that is tracking the US transducer.

The calibration jig can include imagable portions that are positioned within a container. The imagable portions can be positioned so as to allow for a single solution regarding a location of the US transducer relative to the imagable portions. The imagable portions can be placed in a "V" shape where the imagable portions can be identified in the image plane and their distance apart can relate to only one location on the "V" when imaged through the "V".

A verification device can also ensure that the image plane is known relative to the US transducer. Because the tracked locations are known due to tracking of a tracking device positioned relative to the US transducer, if the US transducer moves relative to the tracing device the image plane may no longer be calibrated for tracking or navigation purposes. Thus, a verification device or jig can be used to create an initial verification plane and can be used at a later time to verify that the image plane has not moved relative to the tracking device by ensuring that the US transducer is repeatably placed relative to the verification jig.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIGS. 6A-6C are environmental schematic views of an imaging system in a verification jig, according to various embodiments.

Corresponding reference numerals indicate corresponding parts throughout the several views of the drawings.

DETAILED DESCRIPTION

Example embodiments will now be described more fully with reference to the accompanying drawings. As discussed herein, a cine loop can refer to a plurality of images acquired at a selected rate of any portion. The plurality of images can then be viewed in sequence at a selected rate to indicate motion or movement of the portion. The portion can be an anatomical portion, such as a heart, or a non-anatomical portion, such as a moving engine or other moving system.

Figure 1:
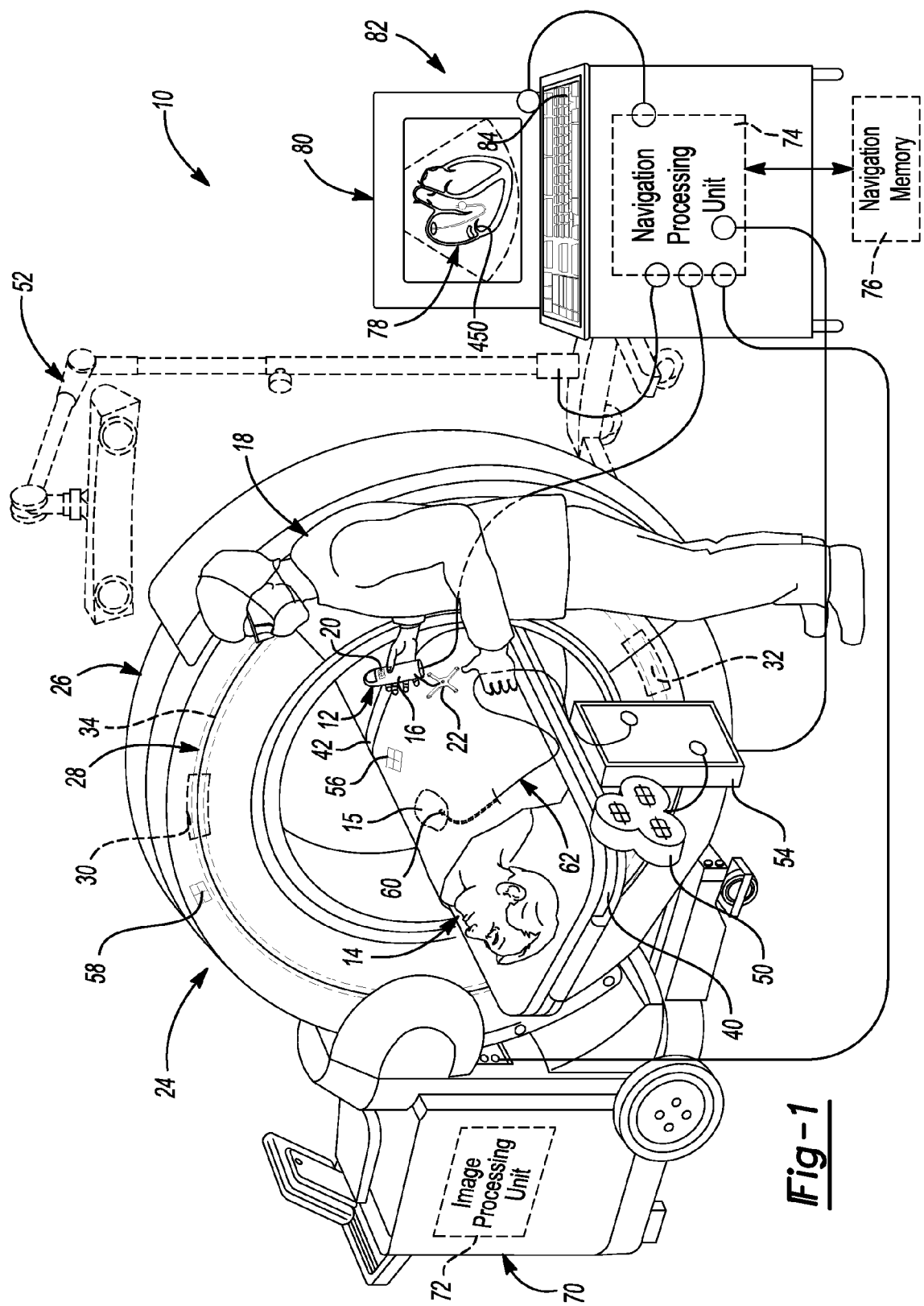
FIG. 1 is an environmental view of a subject with an imaging and navigation system.

FIG. 1 is a diagram illustrating an overview of a navigation system 10 that can be used for various procedures. The navigation system 10 can be used to track the location of an item, such as an implant or an instrument, and at least one imaging system 12 relative to a subject, such as a patient 14. It should be noted that the navigation system 10 may be used to navigate any type of instrument, implant, or delivery system, including: guide wires, arthroscopic systems, ablation instruments, stent placement, orthopedic implants, spinal implants, deep brain stimulation (DBS) probes, etc. Non-human or non-surgical procedures may also use the navigation system 10 to track a non-surgical or non-human intervention of the instrument or imaging device. Moreover, the instruments may be used to navigate or map any region of the body. The navigation system 10 and the various tracked items may be used in any appropriate procedure, such as one that is generally minimally invasive or an open procedure.

The navigation system 10 can interface with or integrally include an imaging system 12 that is used to acquire pre-operative, intra-operative, or post-operative, or real-time image data of the patient 14. For example, the imaging system 12 can be an ultrasound imaging system (as discussed further herein) that has a tracking device 22 attached thereto (i.e. to be tracked with the navigation system 10), but only provides a video feed to the navigation processor 74 (to allow viewing of images on the display device 80). Alternatively, the imaging system 12 can be integrated into the navigation system 10, including the navigation processor 74.

It will be understood, however, that any appropriate subject can be imaged and any appropriate procedure may be performed relative to the subject. The navigation system 10 can be used to track various tracking devices, as discussed herein, to determine locations of the patient 14. The tracked locations of the patient 14 can be used to determine or select images for display to be used with the navigation system 10. The initial discussion, however, is directed to the navigation system 10 and the exemplary imaging system 12.

In the example shown, the imaging system includes an ultra-sound (US) imaging system 12 that includes an US housing 16 that is held by a user 18 while collecting image data of the subject 14. It will be understood, however, that the US housing 16 can also be held by a stand or robotic system while collecting image data. The US housing and included transducer can be any appropriate US imaging system 12, such as the M-TURBO® sold by SonoSite, Inc. having a place of business at Bothell, Wash. Associated with, such as attached directly to or molded into, the US housing 16 or the US transducer housed within the housing 16 is at least one imaging system tracking device, such as an electromagnetic tracking device 20 and/or an optical tracking device 22. The tracking devices can be used together (e.g. to provide redundant tracking information) or separately. Also, only one of the two tracking devices may be present. It will also be understood that various other tracking devices can be associated with the US housing 16, as discussed herein, including acoustic, ultrasound, radar, and other tracking devices. Also, the tracking device can include linkages or a robotic portion that can determine a location relative to a reference frame.

Also shown in FIG. 1 is a second imaging system 24 that comprises an O-arm® imaging device sold by Medtronic Navigation, Inc. having a place of business in Louisville, Colo., USA. The second imaging device 24 includes imaging portions such as a generally annular gantry housing 26 that encloses an image capturing portion 28. The image capturing portion 28 may include an x-ray source or emission portion 30 and an x-ray receiving or image receiving portion 32. The emission portion 30 and the image receiving portion 32 are generally spaced about 180 degrees from each other and mounted on a rotor (not illustrated) relative to a track 34 of the image capturing portion 28. The image capturing portion 28 can be operable to rotate 360 degrees during image acquisition. The image capturing portion 28 may rotate around a central point or axis, allowing image data of the patient 26 to be acquired from multiple directions or in multiple planes.

The second imaging system 24 can include those disclosed in U.S. Pat. Nos. 7,188,998; 7,108,421; 7,106,825; 7,001,045; and 6,940,941; all of which are incorporated herein by reference. The second imaging system 24 can, however, generally relate to any imaging system that is operable to capture image data regarding the subject 14 other than the US imaging system 12 or in addition to a single US imaging system 12. The second imaging system 24, for example, can include a C-arm fluoroscopic imaging system which can also be used to generate three-dimensional views of the patient 14.

The patient 14 can be fixed onto an operating table 40, but is not required to be fixed to the table 40. The table 40 can include a plurality of straps 42. The straps 42 can be secured around the patient 14 to fix the patient 14 relative to the table 40. Various apparatuses may be used to position the patient 40 in a static position on the operating table 40. Examples of such patient positioning devices are set forth in commonly assigned U.S. patent application Ser. No. 10/405,068, published as U.S. Pat. App. Pub. No. 2004-0199072 on Oct. 7, 2004, entitled "An Integrated Electromagnetic Navigation And Patient Positioning Device", filed Apr. 1, 2003 which is hereby incorporated by reference. Other known apparatuses may include a Mayfield® clamp.

The navigation system 10 includes at least one tracking system. The tracking system can include at least one localizer. In one example, the tracking system can include an EM localizer 50. The tracking system can be used to track instruments relative to the patient 14 or within a navigation space. The navigation system 10 can use image data from the imaging system 12 and information from the tracking system to illustrate locations of the tracked instruments, as discussed herein. The tracking system can also include a plurality of types of tracking systems including an optical localizer 52 in addition to and/or in place of the EM localizer 50. When the EM localizer 50 is used, the EM localizer can communicates with or through an EM controller 54. Communication with the EM controller can be wired or wireless.

The optical tracking localizer 52 and the EM localizer 50 can be used together to track multiple instruments or used together to redundantly track the same instrument. Various tracking devices, including those discussed further herein, can be tracked and the information can be used by the navigation system 10 to allow for an output system to output, such as a display device to display, a position of an item. Briefly, tracking devices, can include a patient or reference tracking device (to track the patient 14) 56, a second imaging device tracking device 58 (to track the second imaging device 24), and an instrument tracking device 60 (to track an instrument 62), allow selected portions of the operating theater to be tracked relative to one another with the appropriate tracking system, including the optical localizer 52 and/or the EM localizer 50. The reference tracking device 56 can be positioned on the instrument 62 (e.g. a catheter) to be positioned within the patient 14, such as within a heart 15 of the patient 14.

It will be understood that any of the tracking devices 20, 22, 56, 58, 60 can be optical or EM tracking devices, or both, depending upon the tracking localizer used to track the respective tracking devices. It will be further understood that any appropriate tracking system can be used with the navigation system 10. Alternative tracking systems can include radar tracking systems, acoustic tracking systems, ultrasound tracking systems, and the like. Each of the different tracking systems can be respective different tracking devices and localizers operable with the respective tracking modalities. Also, the different tracking modalities can be used simultaneously as long as they do not interfere with each other (e.g. an opaque member blocks a camera view of the optical localizer 52).

An exemplarily EM tracking system can include the STEALTHSTATION® AXIEM™ Navigation System, sold by Medtronic Navigation, Inc. having a place of business in Louisville, Colo. Exemplary tracking systems are also disclosed in U.S. Pat. No. 7,751,865, issued Jul. 6, 2010 and entitled "METHOD AND APPARATUS FOR SURGICAL NAVIGATION"; U.S. Pat. No. 5,913,820, titled "Position Location System," issued Jun. 22, 1999 and U.S. Pat. No. 5,592,939, titled "Method and System for Navigating a Catheter Probe," issued Jan. 14, 1997, all herein incorporated by reference.

Further, for EM tracking systems it may be necessary to provide shielding or distortion compensation systems to shield or compensate for distortions in the EM field generated by the EM localizer 50. Exemplary shielding systems include those in U.S. Pat. No. 7,797,032, issued on Sep. 14, 2010 and U.S. Pat. No. 6,747,539, issued on Jun. 8, 2004; distortion compensation systems can include those disclosed in U.S. Pat. No. 10/649,214, filed on Jan. 9, 2004, published as U.S. Pat. App. Pub. No. 2004/0116803, all of which are incorporated herein by reference.

With an EM tracking system, the localizer 50 and the various tracking devices can communicate through the EM controller 54. The EM controller 54 can include various amplifiers, filters, electrical isolation, and other systems. The EM controller 54 can also control the coils of the localizer 52 to either emit or receive an EM field for tracking. A wireless communications channel, however, such as that disclosed in U.S. Pat. No. 6,474,341, entitled "Surgical Communication Power System," issued Nov. 5, 2002, herein incorporated by reference, can be used as opposed to being coupled directly to the EM controller 54.

It will be understood that the tracking system may also be or include any appropriate tracking system, including a STEALTHSTATION® TRIA®, TREON®, and/or S7™ Navigation System having an optical localizer, similar to the optical localizer 52, sold by Medtronic Navigation, Inc. having a place of business in Louisville, Colo. Further alternative tracking systems are disclosed in U.S. Pat. No. 5,983,126, to Wittkampf et al. titled "Catheter Location System and Method," issued Nov. 9, 1999, which is hereby incorporated by reference. Other tracking systems include an acoustic, radiation, radar, etc. tracking or navigation systems.

The second imaging system 24 can further include a support housing or cart 70 that can house a separate image processing unit 72. The cart 70 can be connected to the gantry 26. The navigation system 10 can include a navigation processing unit 74 that can communicate or include a navigation memory 76. The navigation processing unit 74 can include a processor (e.g. a computer processor) that executes instructions to determine locations of the tracking devices based on signals from the tracking devices. The navigation processing unit 74 can receive information, including image data, from the imaging system 12 and/or the second imaging system 24 and tracking information from the tracking systems, including the respective tracking devices and/or the localizers 50, 54. Image data can be displayed as an image 78 on a display device 80 of a workstation or other computer system 82 (e.g. laptop, desktop, tablet computer which may have a central processor to act as the navigation processing unit 74 by executing instructions). The workstation 82 can include appropriate input devices, such as a keyboard 84. It will be understood that other appropriate input devices can be included, such as a mouse, a foot pedal or the like which can be used separately or in combination. Also, all of the disclosed processing units or systems can be a single processor (e.g. a single central processing chip) that can execute different instructions to perform different tasks.

The image processing unit 72 can process image data from the second imaging system 24 and a separate first image processor (not illustrated) can be provided to process or preprocess image data from the imaging system 12. The image data from the image processor can then be transmitted to the navigation processor 74. It will be understood, however, that the imaging systems need not perform any image processing and the image data can be transmitted directly to the navigation processing unit 74. Accordingly, the navigation system 10 may include or operate with a single or multiple processing centers or units that can access single or multiple memory systems based upon system design.

In various embodiments, the imaging system 12 can generate image data that defines an image space that can be registered to the patient space or navigation space. In various embodiments, the position of the patient 14 relative to the imaging system 12 can be determined by the navigation system 10 with the patient tracking device 56 and the imaging system tracking device(s) 20,22 to assist in registration. Accordingly, the position of the patient 14 relative to the imaging system 12 can be determined.

Manual or automatic registration can occur by matching fiducial points in image data with fiducial points on the patient 14. Registration of image space to patient space allows for the generation of a translation map between the patient space and the image space. According to various embodiments, registration can occur by determining points that are substantially identical in the image space and the patient space. The identical points can include anatomical fiducial points or implanted fiducial points. Exemplary registration techniques are disclosed in Ser. No. 12/400,273, filed on Mar. 9, 2009, now published as U.S. Pat. App. Pub. No. 2010/0228117, incorporated herein by reference.

Once registered, the navigation system 10 with or including the imaging system 12, can be used to perform selected procedures. Selected procedures can use the image data generated or acquired with the imaging system 12. Further, the imaging system 12 can be used to acquire image data at different times relative to a procedure. As discussed herein, image data can be acquired of the patient 14 prior to the procedure for collection of automatically registered image data or cine loop image data. Also, the imaging system 12 can be used to acquire images for confirmation of a portion of the procedure.

In addition to registering the subject space to the image space, however, the imaging plane of the US imaging system 12 can also be determined. By registering the image plane of the US imaging system 12, imaged portions can be located within the patient 14. For example, when the image plane is calibrated to the tracking device(s) 20, 22 associated with the US housing 16 then a position of an imaged portion of the heart 15, or other imaged portion, can also be tracked.

Calibration System

To calibrate the US imaging system 12, a calibration system including a calibration device or jig 100, as illustrated in FIGS. 2A-2E, can be used. Calibration jig 100 can be positioned relative to the ultrasound transducer housing 16 (herein US housing 16) to image portions within the calibration jig 100, as discussed herein. The calibration jig 100 can generally include a base portion 102 that allows it to be positioned stably on a table or surface 104. It will be understood that the user 18, or another appropriate individual, can operate the ultrasound imaging system 12 relative to the calibration jig 100 by positioning it in an appropriate location. For example, calibration of the US imaging system 12 can be performed at any appropriate time, such as prior to use in an operative setting. Alternatively, it is understood that the calibration jig 100 can be used to calibrate the US imaging system 12 substantially intraoperatively or immediately prior to imaging the patient 14. According to various embodiments, however, the US imaging system 12 can be calibrated at a single time and the calibration is maintained by the US imaging system 12, such as in the memory system thereof, for any subsequent uses of the US imaging system 12.

The base 102 can be interconnected or used to seal a bottom portion or member 106 that is positioned around an external sleeve or carrier 108 that is positioned over a calibration enclosure that can also be referred to as an inner box or container 110. As discussed herein, the internal box 110 can be filled with a selected material, they can mimic the ultrasound transmission of a subject, such as the soft tissue of the patient 14. The material filling the inner box can be an echoic medium. A film or cover 112 can be positioned over the inner container 110 and covered with a sleeve or sealing member 114. During transport or times of non-use of the calibration jig 100, an external cover 116 can be placed over the top member 114. The cover 116 can include external fingers or dog ears 120 and 122 to engage in depressions in the external container 108 or to engage an undersurface 124 of the upper rim 114, as the upper rim 114 may extend beyond an external perimeter of the outer container 108.

A tracking device 140 can be connected to the calibration jig 100. For example, the tracking device 140 can include posts that are fixed to the inner box 110 and optical tracking devices can be fixed to the posts. Alternatively, or in addition thereto, EM tracking devices can be connected to the posts or can be embedded in the inner box 110 or other appropriate portion of the calibration jig 100.

It is understood by one skilled in the art that the ultrasound imaging system 12 emits and receives ultrasound transmissions with an ultrasound transducer (not illustrated). The US transducer can be placed in a fixed manner within the US housing 16, again as understood in the art. The US transmissions are generally within a plane 130 that defines a plane height 130$h$ and a plane width 130$w$, as illustrated in FIG. 2C. The height 130$h$ and width 130$w$ are dimensions of the US imaging plane that extend from the US housing 16. The US plane 130 can also have a thickness 130$t$ that is negligible for calibration purposes and is not considered for the current discussion. Generally the ultrasound plane 130 extends from the US housing 16 at a position relative to the US housing 16 for the height 130$h$ and the width 130$w$. The plane 130 can extend generally aligned with the US transducer. An image acquired with the US plane 130 can appear as illustrated in FIG. 3 including imaged portions, such as imaged calibration portions of the calibration jig 100.

As discussed further herein, a purpose of the calibration jig 100 is to determine or calibrate the position of the US plane 130 relative to the US housing 16 and tracking devices, such as the EM tracking device 20 or the optical tracking device 22, positioned on or in the US housing 16. Once calibrated, the US imaging system 12 is a calibrated imaging system that can be used in further procedures to identify locations of imaged portions relative to the US housing 16 or the tracking devices associated with the US housing 16. For example, the US plane 130 of the calibrated imaging system 12 can be used to image portions of the subject, such as the heart 15 of the patient 14, wherein the heart wall or valve may be an imaged portion.

The following discussion will specifically discuss the optical tracking device 22, but it is understood that tracking any appropriate tracking device is within the scope of the subject disclosure. Further, certain tracking devices, such as the EM tracking device 20, need not require or work only optimally with "line of site" between the tracking device 20 and the related localizer 50. Also, the localizer may transmit a signal or field that is received and/or sensed by the tracking device to determine a location of the tracking device. For example, the EM localocalizer 50 can either receive or emit a field and the EM tracking device 20 can do the other of receive or emit a field to determine a location of the tracking device 20. Also, it is understood that tracking the tracking device 22 allows for a determination of location information including both spatial position and spatial orientation of the tracked tracking device and instrument to which it is attached.

The US plane 130 is generally understood to be the area or volume about which the US transducer, housed in the US housing 16, can acquire image data. The US transducer emits US waves which are reflected by echogenic or echoic materials (for example bone or materials with physical properties similar to bone) and absorbed or allowed to pass through by non-echogenic or anechoic materials (for example purified water or materials with physical properties similar to purified water). As is understood by one skilled in the art, the echo or reflection from echoic materials as opposed to the absorption or non-reflection of anechoic materials is operable to be used to define image data of the subject 14. Thus, determining or calibrating the location of the US plane 130 relative to the tracking device 22 can assist the navigation system 10 in determining locations of imaged portions in subject space even if the image is not otherwise registered to the subject space. Generally, all points within the image plane can be calibrated at a location relative to the US tracking device 22.

In one example, the location of an imaged portion within the US plane 130 can be used to determine the location of the portions within the image relative to the tracking device 22. The calibration device 100 can be used to calibrate the points or locations within the image plane 130 relative to the tracking device 22. Then, an image can later be acquired with the US imaging system 12 within the US plane 130. The later acquired image can include imaged portions, such as of the heart 15, and the location of the imaged portions can be determined relative to the tracking device 22. This relative location of the imaged portion can then be used to determine the location of the imaged portion within the physical subject space by the navigation system 10. The US imaging system 12 can be registered within the navigation space to allow for a determination of a location of the imaged portion relative to any other tracked and registered portion within the navigation space.

Figure 2A:
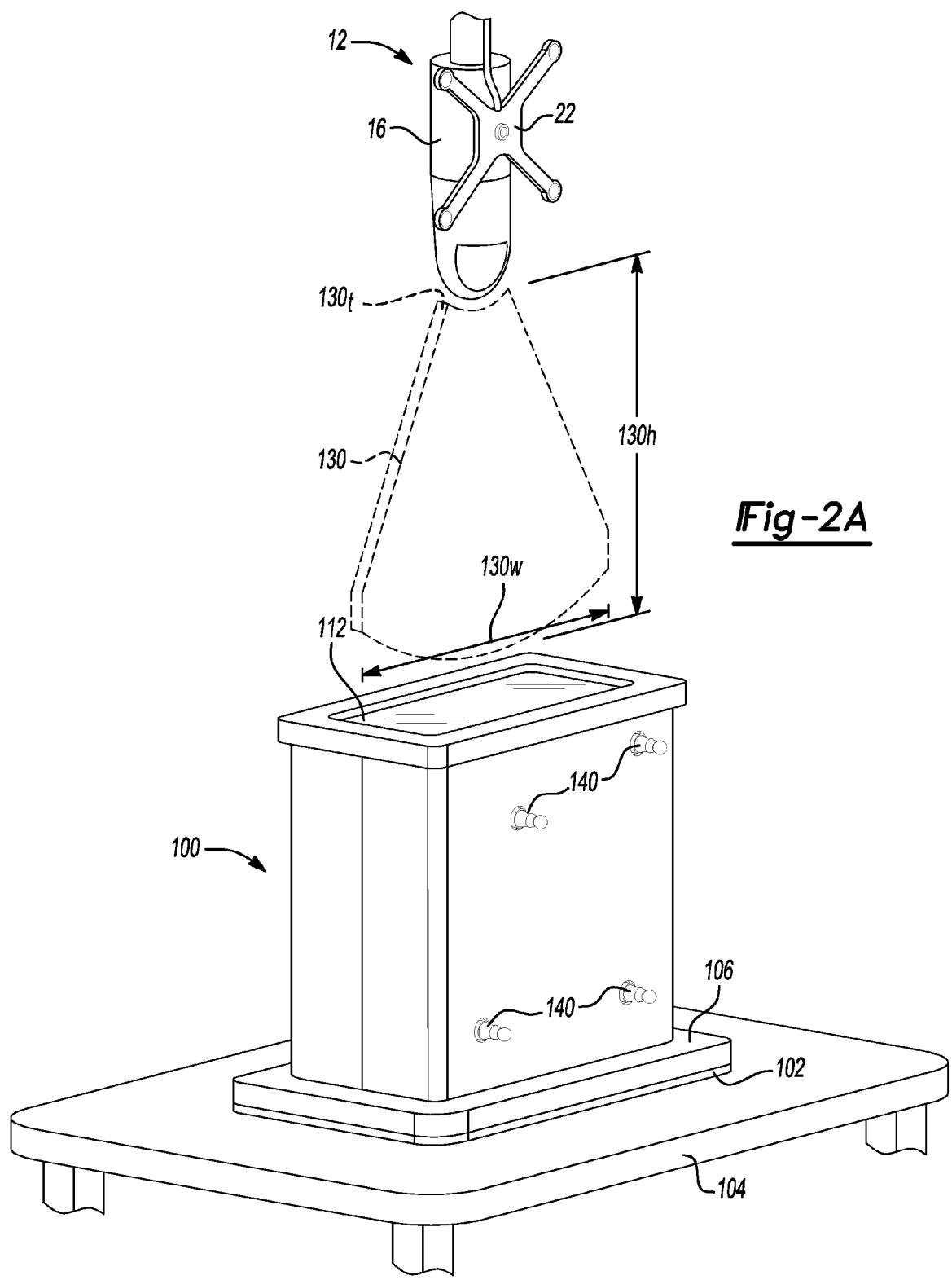
FIG. 2A illustrates a perspective view of a calibration jig according to various embodiments.
Figure 2B:
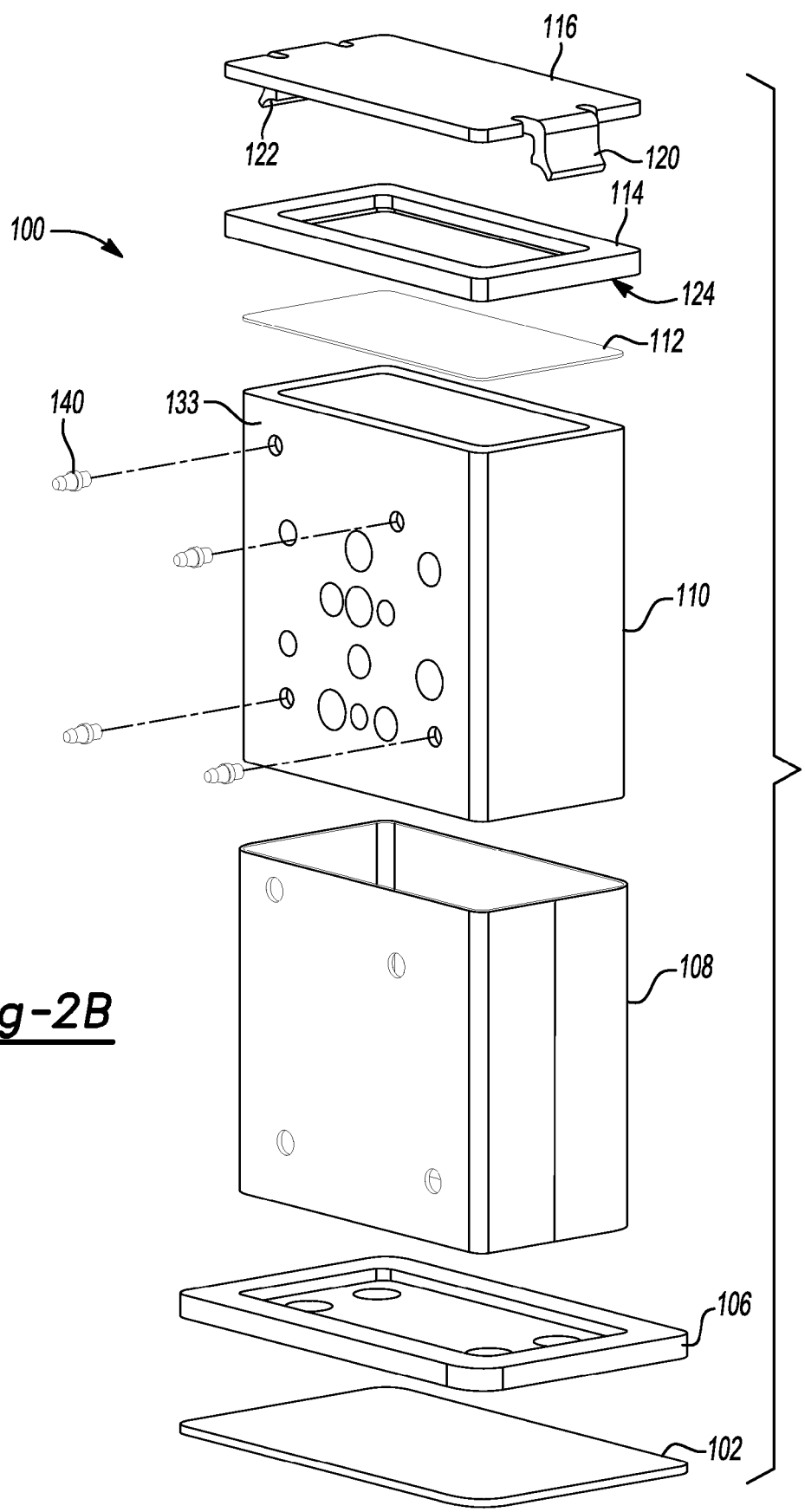
FIG. 2B illustrates an exploded view of the calibration jig of FIG. 2A.
Figure 2C:
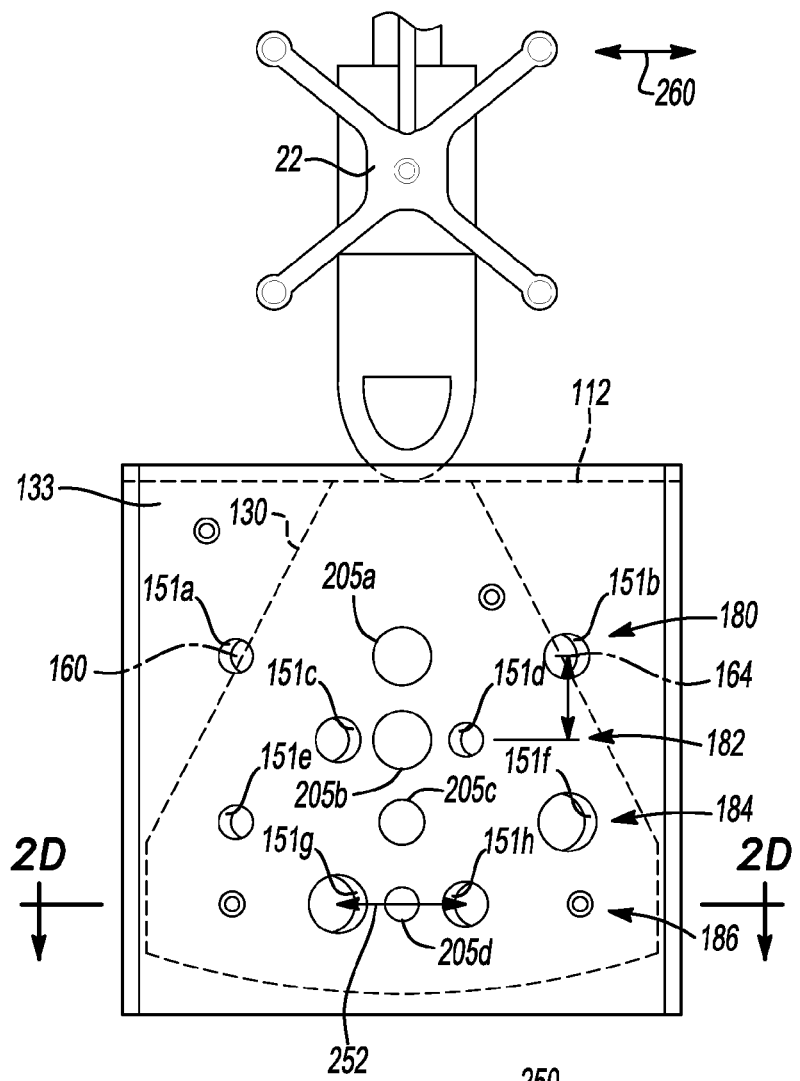
FIG. 2C illustrates a front plan view an internal box portion of the calibration jig of FIG. 2A.
Figure 3:
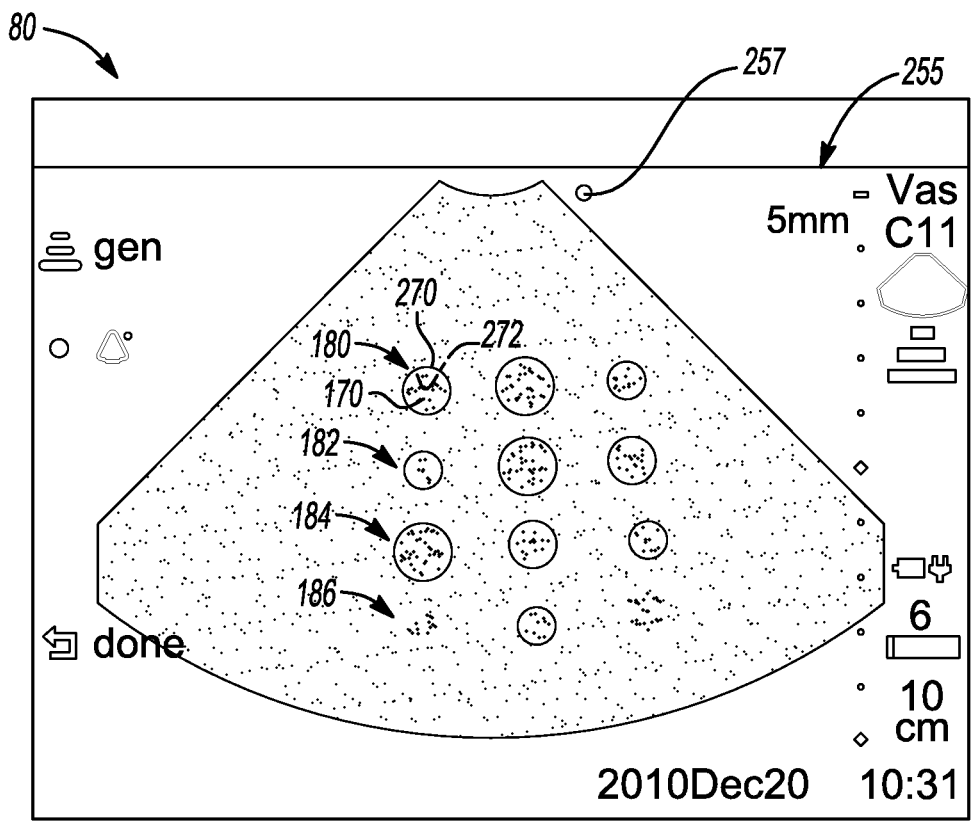
FIG. 3 illustrates a representation of an image taken within the calibration jig of FIG. 2A and displayed on a display device.

In calibrating the US imaging system 12, the US transducer in the US housing 16 can be positioned relative to the calibration jig 100, as illustrated in FIGS. 2A and 2C. Positioned within the inner box 110 can be a plurality of rods, as discussed herein. The rods can be positioned between a front wall 133 and a rear wall 137. In various embodiments the rods can be adhered to a surface of the walls 133, 137 or can be positioned in holes formed in the walls 133, 137. The holes, according to various embodiments, can assist in holding the rods in selected orientations. The following discussion is related to holes within the walls 133, 137, but it is understood that blind holes or depressions, through bores, or no holes can be used.

Figure 2D:
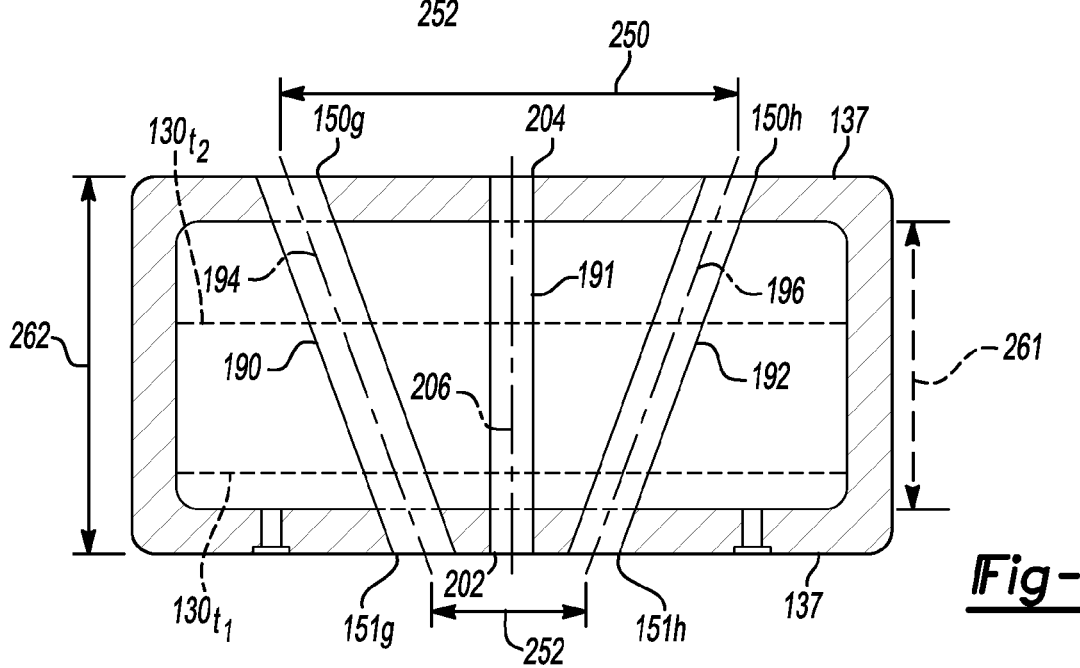
FIG. 2D illustrates a cross-sectional view of the internal box portion along lines 2D-2D of FIG. 2C.
Figure 2E:
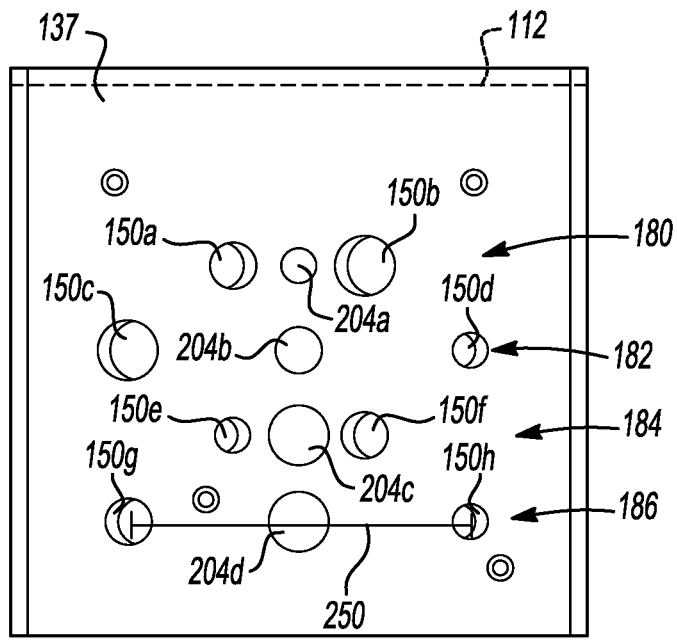
FIG. 2E illustrates a back plan view an internal box portion of the calibration jig of FIG. 2A.

According to various embodiments, holes 150$a$-150$h$, 204$a$-204$d$ define rows 180-186 in the rear wall 137 in the inner box 110, as illustrated in FIGS. 2D and E. Also, corresponding holes 151$a$-151$h$ and 205$a$-205$d$ define corresponding rows in the front wall 133, as illustrated in FIGS. 2B, C, and D. In particular, four rows 180, 182, 184, 186 of two columns of the outer or "V" holes 150 (eight holes 150$a$-150$h$) can be formed in the rear wall 137 of the inner box 110. A column of center holes 204 (four center holes 204$a$-204$d$) are generally aligned in a column between the outer holes 150 in the respective rows 180-186. A plurality of rods 190, 191, 192 are positioned in the holes 150, 204 in the back portion 137 and extend to the corresponding holes 151, 205 in the front portion 133. It will be understood that appropriate rods, similar to rods 190, 191, 192, can be positioned between each pair of respective holes 150,151 and 204,205 but only the row 186 of the holes 150g,150h, 151g,151h and 204d,205d and the rods 190, 191, 192 are described here for simplicity, with reference to FIG. 2C-2E, wherein FIG. 2D is a cross section as defined in FIG. 2C.

With continuing reference to FIG. 2D, rods 190 and 192 are positioned in respective pairs of holes 150g, 150h in the back portion 137 to generally define a "V" shape within the calibration system 100 in the fourth row 186. The "V" shape is defined relative to a plane of the back wall 137 or the front wall 133. The rods 190, 192 extend between the front wall 133 and the back wall 137 by being positioned in holes in the front wall 133 as well. It is understood that the other rows 180-184 can also include rods that are positioned in the respective holes to generally define "V" shapes. In addition, a rod 191 can be positioned in the middle hole 204d in the back portion 137 and extend to a respective hole in the front portion 133. Other middle rods can also be included in the other three rows 180-184. According to various embodiments, each of the different rods in each of the rows can include different diameters or external perimeter areas. Also, the rods can be positioned at differing angles to form the "V" shapes of different angles in each of the rows. For example, the angle between the rod 190 and 192 is about 30 degrees to about 90 degrees, including about 35 degrees to about 50 degrees, and further including about 40 degrees. However, this angle can be selected to be any appropriate angle and may differ in the other rows 180-184.

With reference to FIG. 3, with rods in all of the four rows 180-186 in the calibration jig 100, an image acquired with the US imaging system 12 one location is illustrated. The US system 12 generates the US plane 130 within the calibration system 100 to generate the image illustrated in FIG. 3. As illustrated, three rods are positioned in each of the four rows 180-186 for a total of twelve rods. The rods are formed of an anechoic material, thus appear dark in the image as opposed to the echoic material in the fills the inner box 110. The image plane 130 is generally taken perpendicular to a plane along which the rods 190-192 lie. As illustrated in FIG. 2D the US housing 16 can be moved in the direction of arrow 261 to move the US plane from a first plane location US plane 130t1 to a second plane location US plane 130t2.

In the complete image, illustrated in FIG. 3, all of the rods in the calibration device 100 can be imaged and define calibration portions and/or points spread out in an area of the US plane 130. Having the points spread throughout all or most of an extent of the US plane 130 can assist in confirming accuracy of the calibration. Although, it will be understood that a single point within the US plane 130 can be used to calibrate the US plane 130 relative to the tracking device 22. To determine locations of all points in the US plane 130 interpolation between points including calibration portions can be made.

The US housing 16 can also be moved relative to the calibration system 100 in the direction of an arrow 260 between two sides of the inner box 110, as illustrated in FIG. 2C. As discussed above, the US housing 16 can also be moved in the direction of arrow 261 between the front wall 133 and the back wall 137 of the calibration system 100, as illustrated in FIG. 2D. Image data of the calibration system, including the calibration portions (e.g. the rods in the rows 180-186), is acquired while moving the US housing 16. The acquired image data can be used to calibrate the US imaging system 12, as discussed herein.

As an example of imagable calibration portions that can be used to generate imaged calibration portions, illustrated in FIG. 2D, the fourth row 186 includes the first rod 190 and the third rod 192 with the middle rod 191 therebetween. Each of the rods 190-192 can include respective center axis 194, 206, 196. Center points of each of the rods relating to the center axes 194, 206, 196 can be identified in each plane slice acquired with the US plane 130. Due to the holes 150g,h in the back portion 137 of the inner box 110 a dimension (e.g. a distance) 250 between the centers 194, 196 of the respective rods 190, 192 can be defined. At the front portion 133 of the inner box 110 a second dimension 252 is formed between the centers 194, 196 of the respective rods 190, 192. The two dimensions 250, 252 cause the rods 190, 192 to form a "V" shape within the inner box 110 because the two rods 190, 192 are angled relative to one another at fixed angles between the front wall 133 in the back wall 137. A distance can be determined between the determined centers of the rods that appear as calibration portions in the image data for calibration.

The fixed angles between the two rods 190 and 192 ensures that a distinct dimension between the two rods 190, 192 exists at any single position of the US plane 130 between the front wall 133 and the back wall 137. Thus, when the US plane 130 is moved between the front wall 133 and the back wall 137 in the direction of arrow 261 only a single solution for a position of the plane 130 relative to the row of rods 186 within the calibration system 100 will be determined. Also, the middle rod 191 can be imaged in the image.

The navigation system 10 or separate calibration system (which can include a processor portion and tracking system separate from the navigation system 10) can determine the position of the fourth row 186 of the rods relative to the US housing 16 and the tracking device 22 positioned on the US housing 16. This is based on a known position of the rods in the fourth row 186 relative to the tracking device 140 affixed to the calibration jig 100. The position of the rods relative to the tracking device 22 can be determined based on tracking both the US tracking device 22 and the calibration jig tracking device 140. As discussed herein, once the US plane 130 is calibrated relative to the tracking device 22 a navigation plane, which is the calibrated US plane 130, is known and a position of any imaged portion within the navigation plane can be determined relative to the tracking device 22. Accordingly, the design of the calibration jig 100 with the rods positioned in a manner that allows for only a single solution of the position of the plane 130 relative to the calibration jig 100 and the calibration jig tracking device 140 allows for efficiently identifying the rods within the jig 100 for calibration.

The identification of the specific rods in the rows can be made by identifying the dimension between rods in the same row and dimensions of the different rods (including a pattern of the dimensions, e.g. small, big, medium). As illustrated in FIG. 3, each of the rows 180-186 of rods can be imaged with the US and imaging system 12. The navigation system 10 or appropriate processing system can identify an outer edge or a simulated outer edge 270, for example, of the rods. The outer edge 270 can be used to identify a center 272 of each of the rods using generally known image analysis algorithms. Once edges and/or centers of the rods are identified, the locations of the rods within the image acquired with the US plane 130 can be made.

As understood by one skilled in the art, and discussed above, as the US housing 16 is moved relative to the calibration system 100 and plurality of images for image frames can be acquired relating to the US plane 130. For example, an image can be acquired at the location 130t1 and the location 130t2. At each location the positions of the centers 272 of the rods can be determined within the US plane 130. Based on the determined centers 272 the dimensions between the centers can be determined and this can be used (either alone or in addition to other information, including the dimensions of the rods) to identify the specific rods. The specific rods and their known locations relative the tracking calibration jig tracking device 140 can be used to determine the position of centers (also reference to as calibration portions or points) within the US plane 130 relative to the US tracking device 22. As discussed in relation to a method in a flowchart 400 illustrated in FIG. 5, the position of the centers of the rods are known relative to the inner box 110 and the calibration device tracking device 140 associated therewith. Thus, tracking both the US tracking device 22 and the calibration device tracking device 140 can be used to calibrate the US plane 130 relative to the US tracking device 22.

Once calibrated, the US housing 16 including the US tracking device 22 can be used to identify locations of imaged portions within an image acquired with the US plane 130. As discussed above, the imaged portions can include bones or walls of the heart 15. Accordingly, when an image is acquired with US imaging system 12 a location of an imaged portion within the US plane 130 can be determined with the navigation system 10 based upon the calibrated US plane 130 relative to the US tracking device 22.

Figure 4A:
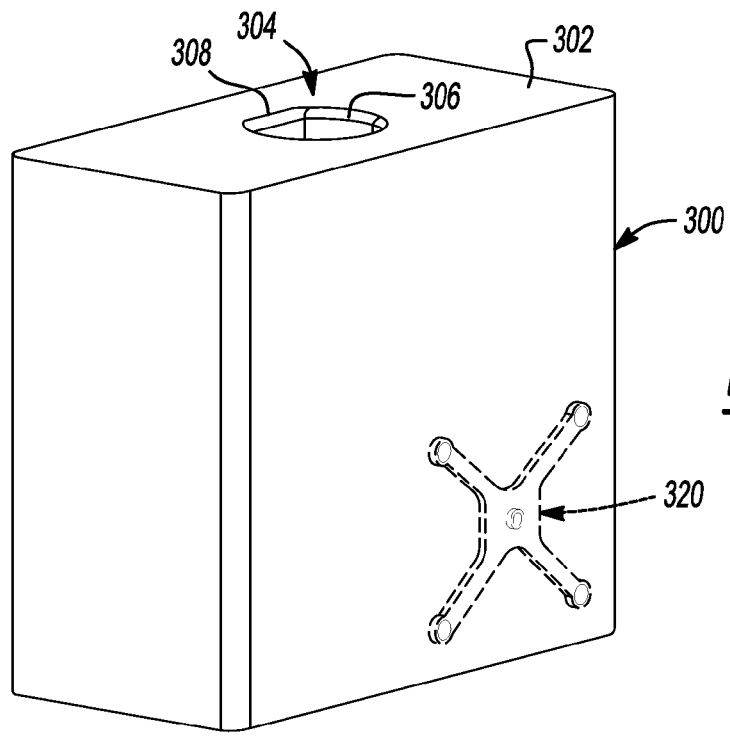
FIG. 4A is a top perspective view of a verification jig.
Figure 4B:
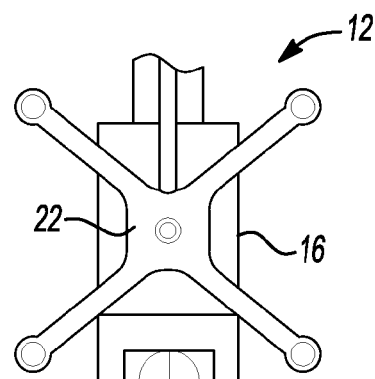
FIG. 4B is a plan view of the verification jig of FIG. 4A including a detail of a housing positioned relative to the verification jig.
Figure 4B:
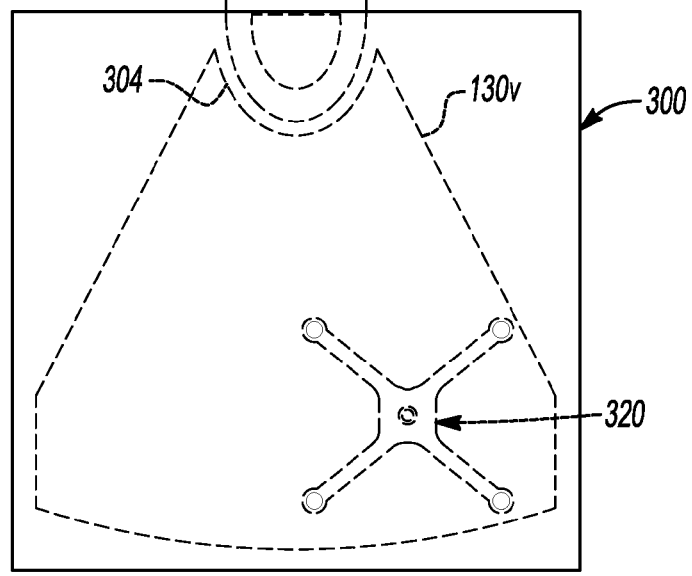

As described herein, the calibration of the US plane 130 can be saved to a memory system of the US imaging system 12 or the navigation system 10. The position of the US plane 130 relative to tracking device 22 can be saved as the navigation plane for use in navigation and comparison with a verification device 300, as illustrated in FIGS. 4A and 4B. The verification device 300 can be used to determine whether the US tracking device 22 has moved relative to the US housing 16 after an initial verification following calibration of the US plane 130.

Verification System

With reference to FIGS. 4A and 4B, the verification device 300 can include a portion or surface configured for interconnection with a portion of the US imaging system 12, for example the US housing 16, with the verification device 300. According to various embodiments, the verification device 300 can include a top surface or wall 302 that defines or includes a US housing engaging portion, such as a depression 304. The depression 304 can include a selected geometry, such as an outer perimeter 306 that substantially tightly engages, such as to constrict movement, with the US housing 16. Additionally, the depression 304 can include a keyed portion, such a flat or keyed area, to engage the US housing 16 in a substantially single orientation relative to the verification device 300. In addition to or alternatively to the depression 304 the US housing engaging portion can be a clamp or holding member can be used to repeatably fix the housing 16 relative to the verification device 300.

The verification device 300 can also include only the top wall 302 and the tracking device 320 can be fixed to the top wall 302. Regardless, the tracking device 320 is generally rigidly positioned relative to the US housing engaging portion, such as the depression 304, in one location. The verification device 300, including a verification member interconnecting the US housing engaging portion and the tracking device 320 is generally inflexible or rigid. The amount or rigidity can be equal to or less than an error amount in tracking by the tracking system. For example, it can be selected to form the verification member to allow for about 0.01 mm to about 5 mm of movement between the US housing engaging portion and the tracking device 320.

During a verification procedure, discussed herein, the US housing 16 can be positioned relative to and/or at least partially within the verification device 300 in a substantially single location. US tracking device 22 can thereby be fixed at a selected and single position and single orientation relative to the verification device tracking device 320 associated with the verification device 300. According to various embodiments, the verification tracking device 320 can be an optical tracking device. It will be understood, however, that the verification device tracking device 320 can be any appropriate tracking device, such as an EM tracking device, acoustic tracking device, or other appropriate tracking device. In addition, it is understood that the verification device 300 can include a plurality of tracking devices operable to allow the verification device 300 to be tracked in a plurality of tracking systems without requiring interchanging of the verification tracking device 320 relative to the verification device 300. Also, the verification tracking device 320 is generally attached to the verification device 300 in a substantially rigid and protected manner. Thus, movement of the verification tracking device 320 relative to the verification device 300 is substantially impractical or impossible.

As illustrated in FIG. 4B, the US housing 16 is positioned at least partially within the verification device 300 and is operable to determine a verification US plane 130v. The verification US plane 130v is the plane that is represented by the US plane 130 of the US imaging system 12 when the US imaging system 12 is positioned in the verification device 300 at least initially when the US plane 130 has been calibrated as the navigation plane of the US imaging system 12. The US plane 130 need not be actually generated with the US transducer to determine the verification US plane 130v, but can be generated if selected. Also, the verification device 300 need not include any imagable portions, rather the verification device tracking device 320 is tracked or known relative to the location of the US tracking device 22.

Based upon the positions of the verification tracking device 320 and the US tracking device 22 the position of the verification US plane 130v can be verified and/or saved relative to the verification device 300 for later use. In other words, the verification plane 130v is an initial position of the US imaging system 12, including the US housing 16, relative to the verification device 300, including the tracking device 320, with a known position of the US tracking device 22 relative to the US housing 16. The known position of the US tracking device 22 relative to the US housing 16 can be based on the calibration jig 100 and use thereof, as discussed above and herein. The verification device 300 can be used to confirm that the US tracking device 22 has not moved relative to the US housing 16 at any selected time after an initial or selected verification. Also, the verification system can be used to translate the US plane to match the verification plane 130v initially determined. Accordingly, by fixing the US housing 16 relative the verification device 300 and tracking the US tracking device 22 and the verification tracking device 320, the verification US plane 130v defined by the US imaging system 12 is known or determined relative to the US tracking device 22 and the verification device tracking device 320.

Because the US transducer is fixed in a single location within the housing, the US imaging system 12 will generate the US plane 130 relative to the housing 16 at only one position. In light of this fixed configuration, it is determined that the US transducer and the US plane 130 relative to the US housing 16 is immutable and unchanging. The position of the tracking device 22, however, may move relative to the housing over time. Thus, only the tracked location of the US tracking device 22 relative to the actual US plane generated with the US imaging system may change.

If the US tracking device 22 moves relative to the housing 16 then the calibrated position of the US plane 130 relative to the US tracking device 22 will become invalid. Thus, once calibration is completed and prior to a movement of the US tracking device 22, the verification plane 130v can be determined. This can be determined, as discussed herein, by tracking the location of the US tracking device 22 relative to the verification device tracking device 320.

The verification plane 130v, therefore, is the determined location of the verification tracking device 320 relative to the calibrated location of the US tracking 22. The calibrated location of the US tracking device 22 is based on calibration of the US plane 130 relative to the US tracking device 22. Generally, the verification plane 130v is used to compare to an imaginary or real image plane from the US imaging system 12. The verification plane 130v can be defined relative to the verification device 300 while the navigation plane 130n can be defined relative to the US tracking device 22.

Calibration and Verification System and Method

The calibration jig 100 and the verification device 300 have been described above. The calibration jig 100 and the verification device 300 can be used together or separately as discussed with reference to the flowchart 400 illustrated in FIGS. 5A and 5B. It can be understood that a calibration process need not immediately precede a verification procedure. However, for the discussion herein, the calibration process can generally be blocks 402 to 428 of the flowchart 400. The verification process can generally be blocks 430 to 500.

Initially, the following discussion in flowchart 400 assumes that an entire procedure of calibrating the navigation plane with the US imaging system 12 and verifying the position of the navigation plane relative to the US housing 16 in an initial verification. It will be understood, however, that calibration and verification can happen separately and individually and be repeated separately and individually as selected. Accordingly, the following discussion of calibration need not be used immediately prior to verification and that verification need not follow immediately after a calibration procedure. Rather, for example, the calibration can occur by a manufacturer or producer of the US imaging system 12 substantially at a factory or prior to delivery of the US imaging system 12. Verification can be performed at the operation site, such as by a final purchaser of the US imaging system 12, to generate the initial verification plane 130v and for later verification of the navigation plane relative to the US housing 16. It is understood, however, that a final user may also perform both calibration and verification.

Prior to the calibration and verification process discussed in relation to flowchart 400 the US imaging system 12 can otherwise be calibrated or prepared for operation with the appropriate tracking system. US imaging system calibration can include the generally understood and used calibration, such as from the SonoNav™ system, sold by Medtronic, Inc., which is integrated with the StealthStation® navigation platforms. Generally, the US imaging system 12 can include or be calibrated to determine the physical size of each pixel in the image data acquired with the US imaging system 12. Measurement tools of the US imaging system 12 can be used to generate or illustrate static scale bars located on the image as well as rulers drawn on the image. For example, a video scale 255 can then be illustrated on the display 80. The video scale 255 can indicate a distance between each hash mark so that a certain physical distance can be determined relative to the scale (e.g. 1 mm, 2 mm, 5 mm, etc.). Also, any appropriate dimension scale bar or bars can be illustrated including vertical, horizontal, depth, etc. Thus, each pixel can have a determined physical size in the image data. Also, a depth and orientation can be determined and a depth and orientation marker 257 can be illustrated on the display 80. The marker 257 can illustrate the orientation of the image and the depth to which image is being acquired.

The calibration procedure can begin in Start block 402 and after beginning the procedure of the flowchart in block 402, the US imaging system 12 can be positioned relative to the calibration jig 100 in block 404. As illustrated in FIGS. 2A and 2C, the US imaging system 12, including the US housing 16, can be positioned relative to the calibration jig 100. In various embodiments, the US housing 16 can engage a cover or top surface (also referred to as the Scanning Surface) 112 of the calibration jig 100. The US imaging system 12 can be used to acquire image data of the calibration jig 100 in block 406. In acquiring image data of the calibration jig 100, the various calibration portions can be imaged, as illustrated in FIG. 3. As is understood, the navigation system 10, or any appropriate calibration processing system and tracking system, can be used to calibrate the navigation plane of the US imaging system 12 using the calibration jig 100. Also, the calibration processor can be any processor portion that executes calibration instructions. The calibration instructions can be instructions that encode an algorithm according to the calibration method embodied in the flowchart 400.

The location of the US imaging system, for example the US housing 16, can be tracked while acquiring the image data of the calibration jig 100 in block 408. As discussed above, various tracking devices, such as the optical tracking device 22 or EM tracking device 20 can be attached to a portion of the US housing 16 to allow for tracking the US housing 16. Accordingly the location of the US housing 16, as a portion of the US imaging system 12, can be tracked. The location of the calibration jig 100 can also be tracked in block 410. The location of calibration jig 100 can be tracked using the calibration jig tracking device 140 associated with calibration jig 100. The tracking device 140 can include appropriate tracking devices, including those discussed above such as optical, EM, acoustic, or other appropriate tracking devices. Regardless, the location of the US housing 16 and the calibration jig 100 can be tracked during the acquisition of the image data in block 406.

Once image data is acquired while tracking the location of both the US imaging system 12 and the calibration jig 100, a decision block can be used to determine if enough image data has been acquired in block 412. The determination of whether or not enough image data has been acquired in block 412 can be based upon a threshold identified by the navigation system 10, the user 18, a factory calibration, or other appropriate techniques. For example, it can be determined that at least 10, 20, 1000, or any appropriate number of data points regarding the calibration portions need be acquired in the image data for a selected calibration. Alternatively, the threshold can relate to a selected number of slices of image data through the calibration jig 100.

If it is determined that enough image data has not been acquired then a NO path 414 can be followed to move the imaging system 12 to a different location relative to the calibration jig 100 in block 416. The imaging system 12 can be moved relative to the calibration jig 100 in any appropriate manner, such as the user 18 moving the housing 16, a robot moving housing 16, or any other appropriate mechanism. Regardless, the US housing 16 can be moved to a different location relative to the calibration jig 100 to allow the acquisition of additional image data.

After moving the US housing 16 to a different location relative to the calibration jig 100 in block 416, the method can loop to block 406 to acquire additional image data, track the location of the US imaging system 12 in block 408, and track the location of the calibration jig 100 in block 410. Then the decision block 412 can again be queried as to whether or not enough image data has been acquired. It is understood that an indication of whether or not enough image data has been acquired can be illustrated on the display device 80 to instruct the user 18. Other appropriate indications can also be provided such, as visual or audio indications. Regardless, when enough image data has been acquired then a YES path 420 can be followed to identify calibration portions in the acquired image data in block 422.

Figure 5A:
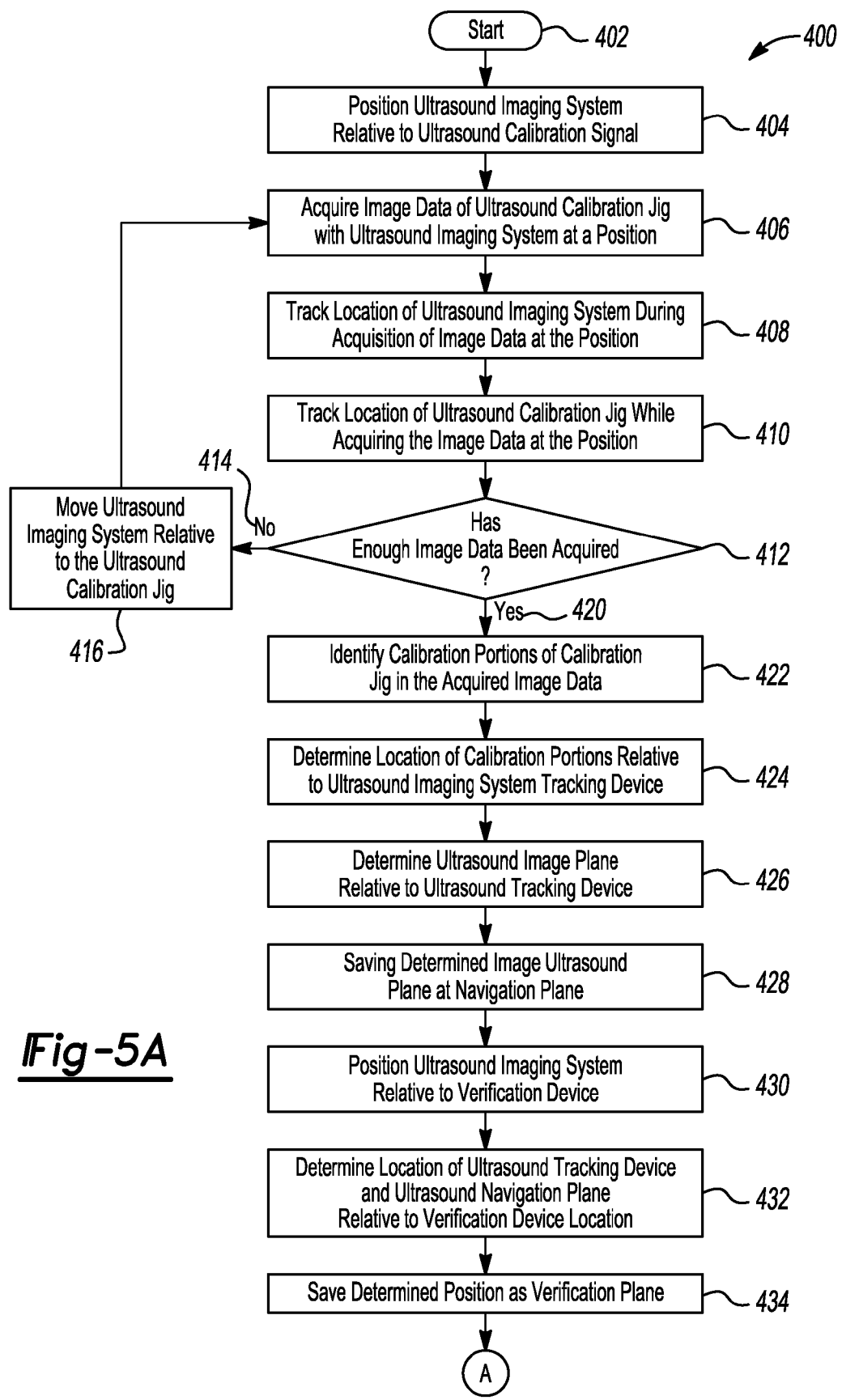
FIGS. 5A and 5B are a flowchart of a method of calibrating and verifying an image plane.
Figure 5B:
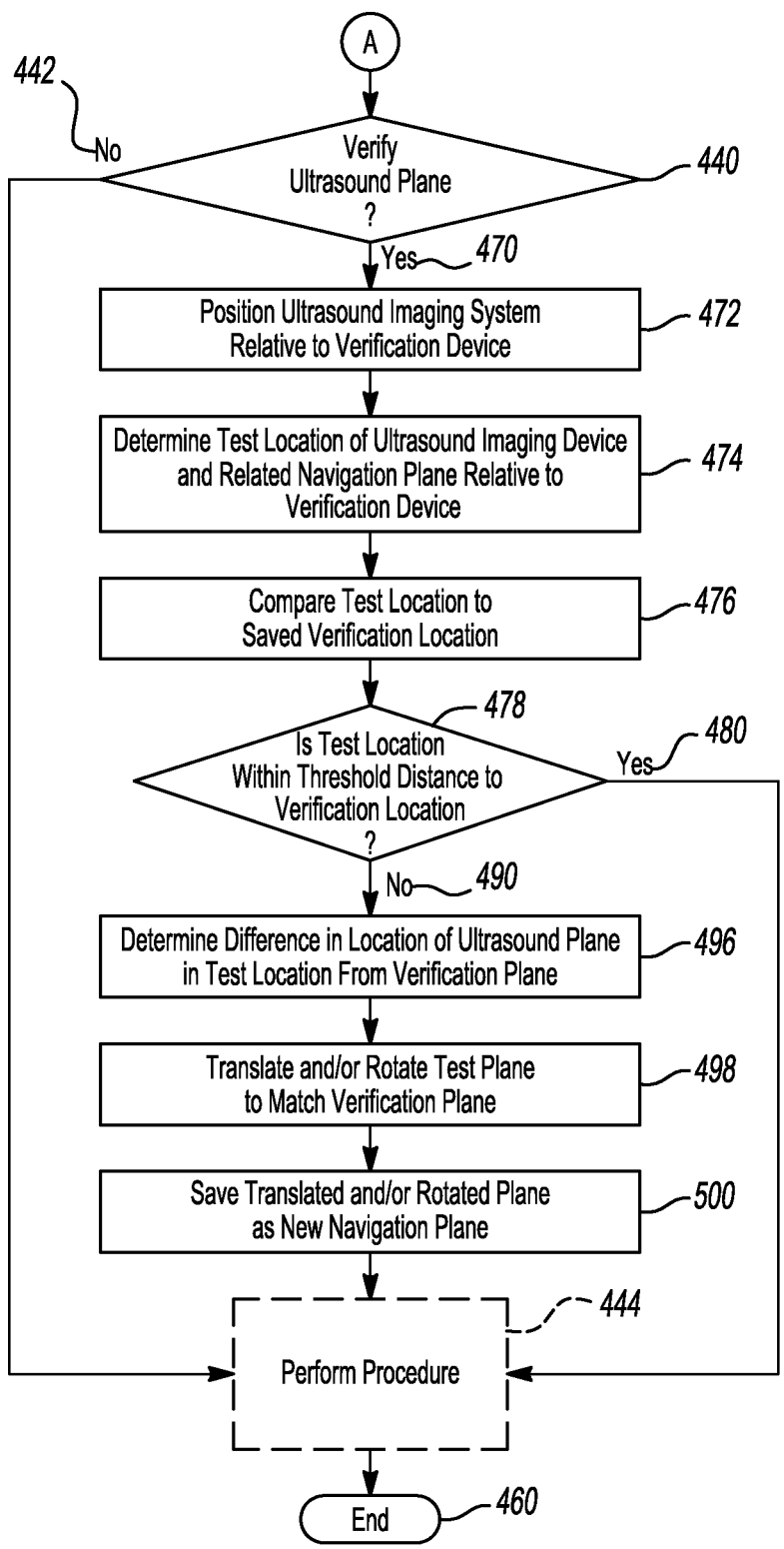

Returning reference to FIG. 3, and continued reference to FIG. 5A, the calibration jig 100 can include one or more anechoic rods that are submerged in an echoic medium. Further the medium (i.e. the material that fills the calibration jig 100) is or can a material that mimics the speed of sound to which the ultrasound transducer is calibrated. For example, the material can mimic the speed of sound through selected portions of an anatomy, such as soft tissue. As illustrated in FIG. 3, the anechoic rods in the echoic medium appear as dark areas on a light background in the image data. Accordingly, the calibration processor system can identify the dark areas in each of the image slices acquired of the calibration jig 100. The calibration system can further identify the outer edge 270 and the centers 272 of each of the rods using generally known edge detection algorithms (e.g. Hough Transform) and/or center detection algorithms (e.g. minimizing algorithms or weighted centroid). The identified portions of the rods can be determined as calibration portions or targets for the calibration process.

The location of the rods in navigation space is known by tracking the calibration jig and the location of the pixels in the image from the US imaging system 12 is known by the US imaging tracking device 22. The location of the US navigation plane relative to the US tracking device 22 in the US imaging system 12 is then determined based on combining the known position of the rods relative to the calibration jig tracking device 140, the determined or tracked location of the calibration jig tracking device 140 (and, thus, the calibration jog 100), the determined centers of the rods in the image, as discussed below, and the tracked location of the US tracking device 22 for the correlation. Any or all of the identification of the rods, the outer edges, or the centers of the rods can be the determined calibration portions targets in the block 422.

After the calibration portions are identified in the image data in block 422 a determination of a location of the calibration portions relative to the US imaging tracking device 22 could be performed in block 424. As an example, the image illustrated in FIG. 3 includes twelve (12) calibration portions that can be identified in block 422. The outer edge or at least a center of each of the calibration image portions can be identified in the image slice illustrated in FIG. 3. The physical space location of each of the calibration portions is previously known relative to the tracking device 140 on the calibration jig 100 based on the physical design and construction of the calibration jig 100. The known location of the calibration portions (which can be the centers of the rods) can be stored for access by the calibration processor. Additionally, the tracked location of the US tracking device 22 is known by tracking the US tracking device 22 with the navigation system 10. Accordingly, the identified calibration portions in the image data can be correlated relative to the tracked location of the tracking device 22 tracked by the navigation system in block 408 during the acquisition of the image data. This allows for determining the location of the calibration portions in the image data relative to the US tracking device 22.

The identification of specific calibration portions can be based on determined dimensions between the calibration portions and sizes of the calibration portions. As illustrated in FIG. 3, the row 186 includes the two outer rods 190, 192 that have larger outer edge dimensions than the middle rod 191. Also, the first rod 190 includes an outer dimension greater than that of the second rod 192. Thus, the relative size of the rods in the row 186 can be used to identify the row 186 as the specific row 186. The centers 191, 194, 196 of each of the rods 190, 191, 192 is known relative to the tracking device 140 based on design and physical characteristics of the calibration jig 100. Also, the dimension between the rods 190, 191, 192 is known at each axial dimension along the rods 190, 191, 192. Thus, when identifying and determining the centers 191, 194, 196 of each of the rods 190, 191, 192 in the US image plane in the image data at least two dimensions of location information can be determined in the image plane data relative to the tracking device 140 based on the image data of the rods in the inner box 110.

The location of portions or points in the image plane 130 can be identified relative to the US tracking device 22 by comparing the determined locations of the calibration portions to the known locations of the calibration portions relative to the calibration jig tracking device 140. The locations of the calibration portions in the navigation space are known by tracking the tracking device 140 in block 410. In other words, the US plane 130, and all of the points therein can be known relative to the location of the US tracking device 22 after determination of the calibration portions in the image data is made in block 424. The locations of points in the US image plane 130 can include interpolation of points between those points specifically identified as calibration image portions.

Determining the US navigation plane can then occur in block 426. The US navigation plane is the plane of points that is imaged in the US plane 130 known relative to the US tracking device 22. The US navigation plane can then be saved in block 428. The US navigation plane can be saved to any appropriate memory system, such as a memory system that is a part of the US imaging system and/or the navigation memory 76.

The US imaging system 12 that is used to generate the US imaging plane 130, which has been calibrated to save a navigation plane 130n (FIGS. 6A-6C), can then be used to image portions, such as portions within the patient 14, and locations of the image portions can be identified within the US navigation plane relative to the US tracking device 22. The known locations of points with the calibrated US plane 130, which can be identified as the US navigation plane, relative to the US tracking device 22 allows for determination of locations of imaged portions relative to the US tracking device 22. Imaged portions can include heart walls, fetal portions, brain structures, or other US imagable portions. Navigated procedures can be any appropriate procedure where an image portion is selected to be identified relative to the US tracking device 22 and therefore can be known within the navigation space of the navigation system 10.

At any appropriate time after the determined US navigation plane has been saved in block 428, the US imaging system 12 can be positioned relative to the verification device 300 in block 430. Accordingly, the calibration process can generally be in blocks 404-428 and the verification method can begin at block 430, as illustrated in FIG. 5A and continuing to FIG. 5B. It is understood that the process can be single process or at least two processes, the calibration process and then the verification process.

As discussed above, and illustrated in FIG. 4B, the US imaging system 12, including the US housing 16, can be positioned relative to the verification device 300 for verifying or determining a verification plane 130v (FIGS. 4B and 6A-6C) of the US imaging system 12. The process of determining the verification plane 130v includes determining a location of the US tracking device 22 relative to the verification tracking device 320 in block 432. As discussed above, the navigation system 10 can track the location of the US tracking device 22 and the verification tracking device 320. Due to the calibrated position of the US navigation plane relative to the US tracking device 22, the tracked location of the US tracking device 22 gives rise to the location of the US verification plane 130v. Generally, the relative location of the US tracking device 22 to the verification tracking device 320 after calibrating the navigation plane of the US imaging system 12 allows for an initial verification plane 130v to be determined. The initial verification plane 130v determination relates to the position of the US tracking device 22 relative to the US housing 16 and/or transducer prior to movement of the US tracking device 22. This also allows for an initial and undisturbed verification or relative location determination of the US tracking device 22 relative to the verification tracking device 320.

In other words, during the calibration, discussed above, the US imaging system 12 can generate the US plane 130 and the original position of the US navigation plane 130n and the tracked location of the US navigation plane 130n can be used for the verification process. Generally, while the US navigation plane 130n is determined or acquired the tracked location of the US imaging system 12 can be performed. A tracked location of the verification device 300 can also be performed when the US navigation plane 130n is known relative to the tracked location of the US imaging system 12. This initial known and tracked location of the navigation plane 130n can be the determined position of the verification plane 130v when the US navigation plane 130n is tracked relative to the verification device 300, initially.

Once a determination of the location of US tracking device 22 relative to the verification tracking device 320 is made in block 432, the determination verification plane 130v can be saved in block 434. The verification plane 130v can be saved to any appropriate memory system, such as the memory system 76. By saving the verification plane 130v in block 434, anytime after the initial verification the US tracking system 12 can be positioned relative to the verification device 300 to confirm that the verification plane 130v remains equivalent to the navigation plane of US tracking system 12. As discussed above, the calibration of the US plane 130 allows for determination of positions within the imaging plane relative to the US tracking device 22. If the US tracking device 22 moves relative to the US housing 16 or the US transducer within the housing then the location of the image plane generated by the US imaging system 12 relative to the US tracking device 22 changes from the calibrated location and the calibration of the navigation plane is no longer accurate.

After the initial verification, when the verification plane 130v is saved, a determination of whether a verification the US plane is desired can be made in block 440. Generally, the determination of whether verification is to occur happens prior to a procedure or use of the US imaging system 12. If no verification is desired or selected, then a NO path 442 can be followed to optionally performing a procedure in block 444. Performing a procedure in block 444 is optional and can include any appropriate procedure. For example, the US imaging system 12 can be used to image a selected portion of the patient 14, such as the heart 15 of the patient. It is understood by one skilled in the art, that the US imaging system 12 can be moved relative to the patient 14 to image portions of the heart 15. Due to the calibration of the US imaging plane 130 positions of imaged portions within the heart 15 can be determined. For example, a location of a right tricuspid 450 can be made, as identified on the display device 80. The identification of a particular portion can be made by the user 18 using the input device 84 and the calibrated US imaging plane 130 can be used to identify the location of the user identified image portion within the navigation space by the navigation system 10. It will be understood that any appropriate procedure can occur and imaging of the brain, bone structures, or other portions of the patient 14 can be made. Alternatively, or in addition to the patient 14, it is understood that nonhuman imaging can occur. For example, imaging of an article of manufacture can also occur. Regardless, after the optional procedure the method can then END in block 460. This can be after performing any selected procedure, steps such as ablating tissue in the heart 15, positioning a probe within the brain of the patient 14, or other appropriate procedure steps.

Alternatively, if the decision in the decision block 440 is to verify the US plane then the YES path 470 can be followed to position the US imaging device 12 relative to, such as in, the verification device 300 in block 472. The US imaging device 12 can be positioned within the verification device 300 as illustrated in FIG. 4B. The verification device used in block 472 is generally the same verification device or another verification device that includes specifications substantially identical to the verification device when determining the initial verification US plane 130v in block 432. As discussed above, the verification device 300 generally includes a portion that can hold or fix the US imaging system, or at least the housing 16, at a location relative to the verification tracking device 320.

Figure 6C:
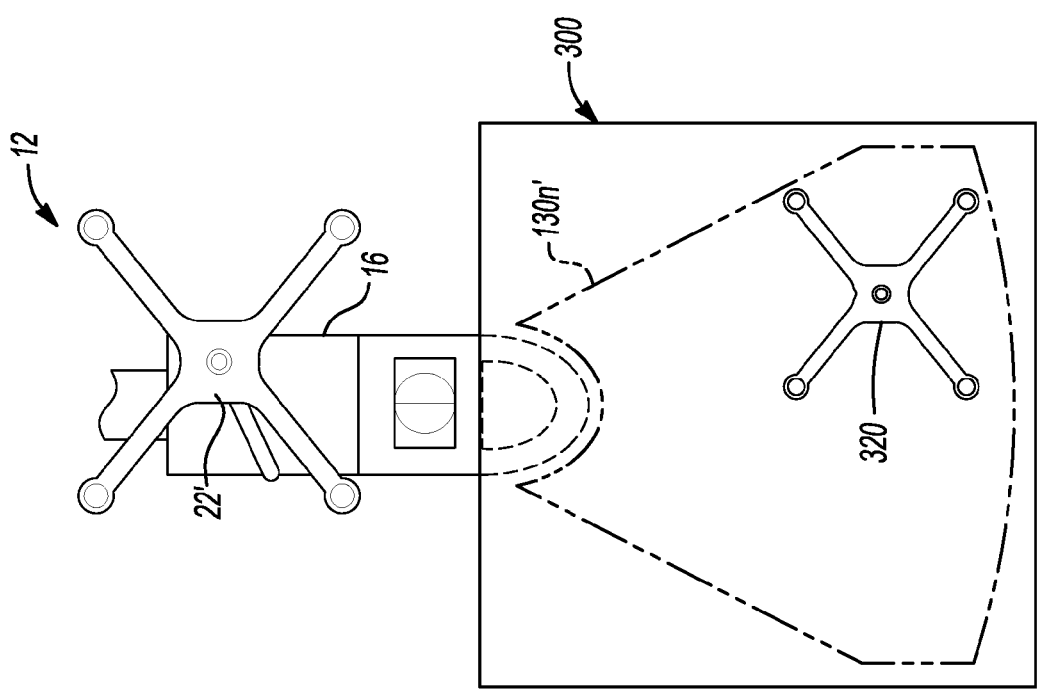

The US imaging device 12 is positioned in the verification device 300 and a determination of a test location of the US imaging device relative to a test location of the verification device is made in block 474. The determined test location of the US imaging device 12 includes or is the tracked location of the US imaging system 12 relative to the verification device 300, as illustrated in FIGS. 6A, 6B, and 6C. Also, because the location of the navigation plane 130n is known relative to the US tracking device 22, the test location of the US imaging device also relates to a determined position of the US navigation plane 130n. The verification device 300 and the US imaging device 12 can be tracked, as discussed above, and the locations of each can be used to determine the test location.

In block 476, the determined test location (e.g. the tracked location of the US imaging device relative to the tracked location of verification device 300) is compared to the saved determined position of the verification plane 130v from block 434. The saved verification plane 130v includes the location of the navigation plane 130n at the initial time relative to the verification device 300. The saved verification plane 130v, inherently, included a position of the US taking device 22 relative to the verification tracking device 320, which are fixed relative to one another due to the positioning of the US imaging system 12 in the verification device 300. Thus, the saved verification plane 130v from block 434 can be compared to the tracked location of the navigation plane 130n which is the test location of the navigation plane from block 474.

A decision of whether the test location is identical to the initial verification location can then be made in block 478. The decision block 478 can include reference to a threshold difference in location. For example, the threshold difference in plane or tracking device relative location can be about 0.1% to about 10%, including about 1%. Alternatively, absolute differences can be used as the threshold difference, such as about 0.1 millimeters (mm) to about 5 mm, including about 0.2 mm to about 0.7 mm, and further including about 0.5 mm can be used as the threshold difference.

To determine if the threshold difference has been passed the US housing 16 is positioned within the verification device 300, as illustrated in FIG. 6A. As exemplarily illustrated in FIG. 6A, the US tracking device 22 has not moved the US tracking device 22 is at a substantially same location relative to the verification to tracking device 320 as illustrated in FIG. 4B. Accordingly, the US verification plane 130v can overlap the navigation plane 130 of the US imaging system 12 and the YES path 480 can be followed to perform the optional procedure in block 444 and then to the END block 460. Generally, as illustrated in FIG. 6A, when the navigation plane 130 and the verification plane 130v overlap the plane of the US imaging system 12 is in the same position as the calibrated position and locations of image portions within the imaging plane can be determined correctly relative to the US tracking device 22 of the US imaging system 12.

With reference to FIG. 6B, if the US tracking device is in a different location, as illustrated by US tracking device 22', then the NO path 490 can be followed from the decision block 478. As illustrated in FIG. 6B the US navigation plane 130 and is at a different location from the US verification plane 130v. This is due to movement of the US tracking device 22 relative to the US housing 16 and/or the US transducer within the US housing 16. Due to the movement of the US tracking device 22 the tracked location of the US navigation plane 130 is at a different location from the initial calibrated position. Therefore, the US navigation plane 130 is at a different location relative to the verification plane 130v than was initially determined with the verification device 300 and does not overlap the verification plane 130v.

As illustrated in FIG. 6B, the navigation plane 130n is theoretically translated in the direction of arrow 492. It will be understood, however, the movement of the US tracking device 22' relative to the US housing 16 can be any movement, such as rotation and/or translation. Regardless, and determination of the difference in the location of the US plane 130n in the test location from the verification plane 130v is made in block 496. The amount of translation and/or rotation can be determined in block 496 due to a tracked difference in location between the US tracking device 22' and the verification tracking device 320 relative to the initially tracked location of the US tracking device 22 relative to the verification tracking device 320.

Once the amount of translation and/or rotation is made, then the US plane at the test location can be translated and/or rotated to match the verification plane 130v in block 498, as illustrated in FIG. 6C, or vice versa. Generally, the verification plane 130v that is saved in block 434 is transformed (i.e. translated and rotated) from the verification device 300 space to the navigation space of the US imaging system 12. The translated and/or rotated test plane can then be saved as a new navigation plane 130n' (where the new navigation plane 130n' can be substantially identical to the original navigation plane 130n in position relative to the US tracking device 22, but only saved after later verification) in block 500. The new navigation plane in block 500 can be used as the navigation plane when navigating a procedure and for determining a location of image portions within the US imaging plane. Thus, the new navigated plane is substantially identical relative to the US tracking device 22 as the calibrated plane and can be reconfirmed using the calibration device 100 in the process discussed above. Generally additional calibration is not necessary due to comparison to the previously saved verification plane 130v using the verification device 300.

The verification device 300 includes the verification device tracking device 320 that is substantially immovable and fixed relative to the holding portions 304 of the verification device 300. Thus, a tracked location of the US imaging system 12 relative to the verification device 300 can be compared to any other tracked location of the US imaging system relative to the verification tracking device 320 when the US imaging system 12 is placed in the holding portion 304. Due to the US imaging system 12 being positioned at a fixed and non-changeable location relative to the verification device 300, a later determination of the location of the US tracking device 22 relative to the verification tracking device 320 can be made that is directly comparable to any other tracked location between the two tracking devices 22, 320. A location change, if any, including both or only one of translation and rotation, can be determined. The amount of translation and rotation can then be calculated to determine the relative location of the US imaging plane relative to the US verification plane 130v. Accordingly, a substantially quick and efficient mechanism to determine the location of the actual US imaging plane relative to the US tracking device 22' can be made at any time. It can be verified that the US imaging plane is either unchanged or the US imaging plane can be easily translated or rotated based upon a calculation for continued navigation to track locations of portions being imaged.

Once the US imaging plane has been saved in block 500 that optional procedure can be performed or continued in block 444. As discussed above, the procedure being performed can be any appropriate procedure including imaging portions of the patient 14 and performing procedures and the patient 14, such as tissue ablation in the heart 15. Specific examples include, tracking or determining tissue shift, such as brain shift, after cranial access. The tracked plane for the US imaging system 12 can be used to determine the location of a portion of the brain at any selected time (e.g. using edge detection or user analysis of the acquired US image). Other examples include identifying or understanding tumor progression and/or removal and implant placement. Images can be acquired of the anatomy during a procedure to ensure proper placement of the implant or for proper resection of a tumor. The procedure can then end in block 460.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. An imaging verification system, comprising:
   a verification device, including:
   a rigid member having an imaging system holding region fixed relative to the rigid member;
   a verification tracking device fixed at a selected location relative to the rigid member;
   an imaging system including:
   a transducer configured to generate an image plane in which an object is imaged;
   an imaging system tracking device connected relative to the transducer at a first position, wherein the imaging system is fixable relative to the verification device at a first time, wherein the imaging system further has a calibrated navigation imaging plane at a selected location, and wherein the navigation imaging plane is at a known location relative to the imaging system tracking device fixed to the imaging system;

a tracking system operable to track the verification tracking device and the imaging system tracking device at least at the first time; and a processor system;

a memory system;

wherein the processor system is configured to execute instructions to determine a verification plane at a determined verification location of the navigation imaging plane relative to the verification device based on the tracked location of both the imaging system and the verification device at the first time, wherein the verification plane includes at least one of a location of the image plane of the imaging system relative to the verification device or a location of the imaging system tracking device relative to the verification tracking device; and wherein the determined verification imaging plane is saved with the memory system;

wherein the imaging system is removable from the verification device and operable to be fixed at the selected location relative to the verification device at a second time after the first time;

wherein the tracking system is configured to track both the imaging system tracking device fixed relative to the imaging system and the verification tracking device fixed relative to the verification device at the second time to determine an imaging plane location at the second time; and wherein the processor system is configured to execute instructions to determine if the imaging plane location at the second time matches the verification plane within a threshold difference.

2. The imaging verification system of claim 1, wherein the holding region includes a keyed depression formed in the rigid member.

3. The imaging verification system of claim 1, wherein the holding region includes a clamp member to fixedly engage the imaging system and hold the imaging system relative to the verification device.

4. The imaging verification system of claim 1, wherein a distance between the imaging system holding region and the verification tracking device fixed at a selected location relative to the rigid member is able to move less than or equal to an amount that is an error of the tracking system.

5. The imaging verification system of claim 1, further comprising:

a display device to display image data acquired with the transducer and illustrate a location of an imaged portion in the image plane based at least in part on the determined position of the image plane relative to the verification device.

6. The imaging verification system of claim 1, wherein the transducer is an ultrasound transducer.

7. The imaging verification system of claim 1, wherein the tracking system is at least one of an optical tracking system, an acoustic tracking system, an electromagnetic tracking system, and a radar tracking system.

8. A method of verifying a location of an image plane of an imaging system, comprising:

positioning an imaging system at a selected fixed location relative to a verification device at a first time;

tracking both the imaging system and the verification device at the first time;

determining a first imaging plane that includes a position of the first imaging plane at least relative to the verification device to be used as a verification plane of the imaging system, with a verification processor system, relative to the verification device based at least in part on the tracked location of both the imaging system and the verification system;

saving the determined first imaging plane in a verification memory system;

positioning the imaging system at the selected fixed location relative to a verification device at a second time after the first time;

operating a tracking system to track both the imaging system and the verification device at the second time;

operating a processor system to determine a second imaging plane that includes a position of the second imaging plane of the imaging system relative to the verification device based at least in part on the tracked location of both the imaging system and the verification device at the second time; and operating the processor system to compare the position of the first imaging plane and the position of the second imaging plane;

wherein the first imaging plane includes information regarding a location of the image plane of the imaging device relative to the imaging device tracking device.

9. The method of claim 8, further comprising:

operating the processor system to determine if the position of the first imaging plane and the position of the second imaging plane are within a selected threshold distance, if the first imaging plane and the second imaging plane are different in an amount greater than the threshold then:

determining a transformation of the first imaging plane and the second imaging plane; and transforming the second imaging plane to match the first imaging plane;

wherein the transformed second imaging plane includes a position substantially identical to the position of the first imaging plane;

saving the transformed second imaging plane as a navigation plane.

10. The method of claim 9, wherein the difference between the first imaging plane and the second imaging plane beyond the threshold is based on movement of an imaging system tracking device associated with the imaging system from a first location at the first time to a second location at the second time.

11. The method of claim 9, further comprising:

tracking the imaging device;

acquiring image data with the imaging device while tracking the imaging device; and determining a location of an imaged portion with the image data relative to the imaging device tracking device based on the saved navigation plane.

12. The method of claim 11, further comprising:

displaying the acquired image data;

selecting the imaged portion, wherein the determined location is of the selected image portion; and displaying the determined location of selected image portion.

13. The method of claim 8, wherein positioning an imaging system at a selected fixed location relative to a verification device at a first time and positioning an imaging system at the selected fixed location relative to a verification device at a second time includes placing a housing member housing an ultrasound transducer in a keyed depression in the verification device wherein the housing member engages the keyed depression in a single position and orientation relative to the verification device.

14. The method of claim 8, wherein tracking both the imaging system and the verification device at the first time includes determining an imaging system location of the imaging system and determining a verification device location of the verification device.

* * * * *